(12) United States Patent
Kim et al.

(10) Patent No.: US 6,430,445 B1
(45) Date of Patent: Aug. 6, 2002

(54) ANTI-AGING ELECTROMAGNETIC APPARATUS

(76) Inventors: Hyun Jong Kim; Ki Suk Kim, both of 3699 Wilshire Blvd. #220, Los Angeles, CA (US) 90010

( * ) Notice: Subject to any disclaimer, the term of this patent is extended or adjusted under 35 U.S.C. 154(b) by 64 days.

(21) Appl. No.: 09/710,652

(22) Filed: Nov. 13, 2000

(51) Int. Cl.⁷ .................................................. A61F 2/00
(52) U.S. Cl. ............................ 607/100; 607/2; 600/13
(58) Field of Search ................................ 607/100, 108, 607/109, 110, 111, 2, 80, 90, 91; 600/13, 14

(56) References Cited

U.S. PATENT DOCUMENTS

| | | |
|---|---|---|
| 5,643,322 A | * 7/1997 | Ito et al. .......................... 607/2 |
| 5,649,972 A | * 7/1997 | Hochstein .................... 607/100 |
| 5,906,812 A | 5/1999 | Richard et al. |
| D410,810 S | 6/1999 | Lozier |
| 5,976,558 A | 11/1999 | Richard et al. |
| 5,996,780 A | 12/1999 | Gurrera |
| 6,022,548 A | 2/2000 | Corey et al. |
| 6,077,520 A | 6/2000 | Tominaga |
| 6,110,966 A | 8/2000 | Pollock |
| 6,155,966 A | * 12/2000 | Parker .......................... 600/13 |

FOREIGN PATENT DOCUMENTS

| | | | |
|---|---|---|---|
| JP | 58102902 A | * | 6/1983 |
| JP | 04269635 A | * | 12/1992 |

* cited by examiner

*Primary Examiner*—Chen-Wen Jiang

(57) ABSTRACT

An anti-aging device to control the level of oxidation occurring at skin surface is described. The device is plugged into an electrical outlet to allow electromagnetic waves to pass through the inner surface, which has been pre-treated with far infrared light. The resulting affect on the skin is the reduced appearance of wrinkles and other signs of aging.

2 Claims, 1 Drawing Sheet

ANTI-AGING ELECTROMAGNETIC APPARATUS

FIELD OF THE INVENTION

The present invention generally relates to an anti-aging apparatus, which produces electromagnetic waves through a material specially treated with far infrared light and can be used with a source of electric power.

BACKGROUND OF THE INVENTION

Many products and devices exist out in the market that claim to slow, stop or reverse the aging process of the skin. Particularly common are the topical creams for face or body, mud or clay treatments and vitamin E supplements, one of the many anti-oxidants that occur in nature. Electronic devices for such similar purposes exist as well. These include facial saunas, and body wraps and other forms of topical stimulation.

The present invention is not applied to the skin like lotion nor does it make any obvious contact with the skin. The present invention affects the skin's surface by means of changing the condition of the environment as in decreasing the amount of oxygen by a trace amount on the skin's surface so that less oxidation is allowed to take place.

Humans need oxygen to survive yet oxygen in its "bad" form is the element that can cause disease, aging and eventually death. When we breathe, we undergo a process of taking fuel, the food we eat, and converting it into heat and carbon dioxide. Oxidation is a naturally occurring event in our bodies. One of the byproducts of this process, however, is the build up of free oxygen radicals in the presence of moisture. This is an oxygen molecule with an unpaired electron, which is thereby unstable and seeks to find an electron so that it can regain stability. In the process of doing so, the free oxygen radical disturbs many other cells and elements in the body and causes damage. Free radicals are thought to be the cause of more than 60 different diseases including atherosclerosis, cancer, cirrhosis, and Parkinson's disease.

Therefore there is presently a need for the novel features possessed by the present invention. Not only for the purpose of slowing the aging process but for possible health benefits as well.

BRIEF SUMMARY OF THE INVENTION

The present invention is an anti-aging apparatus that uses Electromagnetic waves through a material treated with Far Infrared Light in order to reduce the oxidation level and decrease a trace amount of oxygen on the surface of the skin and thereby reduce free oxygen radicals, which has been proven to be responsible for the aging process.

The present invention is an apparatus having an elliptical hemisphere shape on one end and a connection to an electrical power source at the other end, including but not limited to electric plug outlet, car cigarette adapter, or simply direct contact by means of an adhesive. The elliptical shape is significant because an ellipse has two foci, which is the same distance away from the points that make up the ellipse, as if two circles have been combined. The plug into the outlet comprises two prongs, which receive energy and transmit it to the far infrared treated material including but not limited to polyethylene. The elliptical sphere shape allows the two prongs to administer an equal and consistent amount of electromagnetic waves into the inside cavity of the device and eventually out into the environment.

Once the apparatus is plugged into and energy source electromagnetic waves will be emitted out the other end through material that has been treated with far infrared light, thereby making the environment around the device, such as a room or a car, suitable for anti-aging effects. This is achieved through the slight reduction of oxygen levels at the skin's surface. The far infrared light infused Electromagnetic waves cause the slightly negatively charged electron cloud around the skin's surface to become even more charged thereby reducing oxidation since oxidation is defined as any reaction involving a loss of electrons. This leads to a decrease in the level of free oxygen radicals, which is the cause of aging. The result of consistent use is the measurable effect of less wrinkles and fine lines, more resilience in the skin, and an overall healthier and younger appearance of skin.

BRIEF DESCRIPTION OF THE DRAWINGS

For a better understanding of the nature of the present invention, reference should be made to the following detailed description taken in connection with the accompanying drawings wherein.

DETAILED DESCRIPTION OF THE PREFERRED EMBODIMENT

The present invention utilizes a multi-step process that comprises a plurality of batch processes wherein the product yielded from a step in the overall process is then successively used as the feed for the subsequent batch process.

Once first batch process involves the exposure of the material, including but not limited to, polyethylene to far infrared light. This side will be the side that is not exposed to the environment but is rather in the inner part of the device itself.

The exact duration of the exposure may vary and the effects of the far infrared light up on the inner cavity of the device are proportional to the duration of exposure. This step yields a device of the following equation.

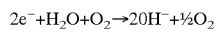

$$2e^- + H_2O + O_2 \rightarrow 2OH^- + \tfrac{1}{2}O_2$$

Therefore, this irradiation of far infrared light induces an oxygen deficiency on the skin. The equation also teaches generation of OH-, the alkaline. Slight alkalinity on the skin also reduces the aging process. The above surface reaction reduces the level of free oxygen radical and oxygen on the human cell. The reverse affect is incurred on the opposite side of the material, or the environment within reasonable proximity to the working device.

Figure 1:
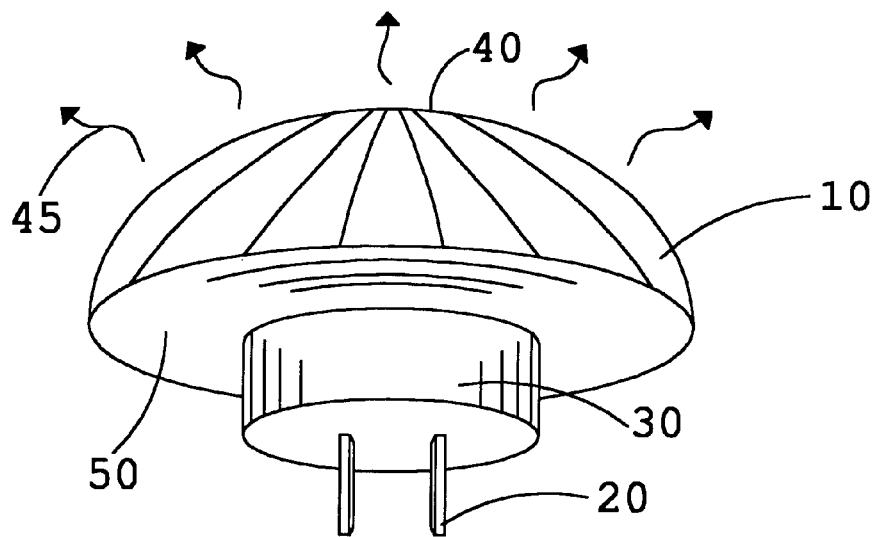
FIG. 1 is a perspective view of the present invention.
Figures 1A, 1B:
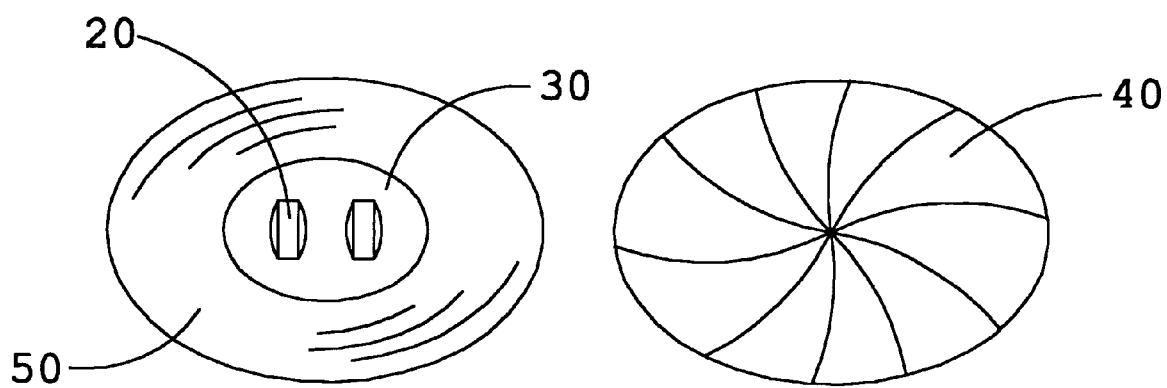
FIG. 1a is bottom view of the present invention.
FIG. 1b is a top view of the present invention.

Referring now to FIG. 1, the preferred embodiment of the present invention comprises a elliptical hemisphere generally referred to as 10 with outer surface 40. The side of portion 40 which faces the inside of the elliptical hemisphere has been treated with far infrared light so that when electromagnetic waves 45 are emitted from surface 40, it will induce the aforementioned reactions. Said elliptical hemisphere 40 is joined to horizontally disposed cylinder 30 which connects sphere 40 with metal prongs 20 which are to be inserted into an outlet. Said cylinder portion of said anti-aging apparatus is centrally located in relation to the ellipse formed by the flat side 50 of elliptical hemisphere 10 so that the ends of prong 20 represent roughly the location of the foci of flat portion 50 as shown in FIG. 1a. FIG. 1b shows rounded surface 40 of said elliptical hemisphere 10.

What is claimed is:

1. An apparatus for anti-aging by way of decreasing the level of oxygen on skin surface in trace amounts in order to decrease the level of oxidation and production of free oxygen radicals comprising:

a polyethylene surface treated with far infrared light on the side that faces the inside of the device and another end to connect to an energy source, said polyethylene surface contact to the skin surface, whereby the level of oxidation is decreased.

2. An anti-aging apparatus according to claim 1, wherein said inner side of the device is subjected to a plurality of successive exposures of varying wavelengths of far infrared light.

* * * * *